United States Patent
Harada et al.

(10) Patent No.: US 6,841,681 B2
(45) Date of Patent: Jan. 11, 2005

(54) PROCESS FOR PRODUCING QUINOLINE CARBOXYALDEHYDE DERIVATIVE AND INTERMEDIATE THEREOF

(75) Inventors: Katsumasa Harada, Yamaguchi (JP); Shigeyoshi Nishino, Yamaguchi (JP); Kenji Hirotsu, Yamaguchi (JP); Hidetaka Shima, Yamaguchi (JP); Naoko Okada, Yamaguchi (JP); Takashi Harada, Yamaguchi (JP); Akira Nakamura, Yamaguchi (JP); Hiroyuki Oda, Yamaguchi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/468,062

(22) PCT Filed: Feb. 14, 2002

(86) PCT No.: PCT/JP02/01261

§ 371 (c)(1),
(2), (4) Date: Aug. 14, 2003

(87) PCT Pub. No.: WO02/064569

PCT Pub. Date: Aug. 22, 2002

(65) Prior Publication Data

US 2004/0077866 A1 Apr. 22, 2004

(30) Foreign Application Priority Data

Feb. 14, 2001 (JP) .................................. 2001-036357

(51) Int. Cl.$^7$ .................... C07D 215/14; C07D 215/12; C07C 255/17; C07C 225/22
(52) U.S. Cl. ....................... 546/173; 546/173; 546/176; 558/414; 564/328
(58) Field of Search ................................ 546/173, 176; 558/414; 564/328; 514/311, 648, 344, 579

(56) References Cited

U.S. PATENT DOCUMENTS 5,011,930 A * 4/1991 Fujikawa et al. ........... 546/101

FOREIGN PATENT DOCUMENTS

| EP | 0 304 063 | 8/1988 |
| EP | 304063 | 2/1989 |
| EP | 0 304 063 | 2/1989 |
| JP | 1-279866 | 11/1989 |
| WO | 00/05213 | 2/2000 |

* cited by examiner

Primary Examiner—Ceila Chang
Assistant Examiner—Janet L. Coppins
(74) Attorney, Agent, or Firm—Oblon, Spivak, McClelland, Maier & Neustadt, P.C.

(57) ABSTRACT

2-Cyclopropyl-4-(4'-fluorophenyl)quinoline-3-carboxyaldehyde useful as a material for pharmaceutical products, can be obtained by reacting 3-cyclopropyl-3-oxopropanenitrile with 2-amino-4'-fluorobenzophenone to obtain 2-cyclopropyl-4-(4'-fluorophenyl)quinoline-3-carbonitrile, and reducing it.

8 Claims, No Drawings

PROCESS FOR PRODUCING QUINOLINE CARBOXYALDEHYDE DERIVATIVE AND INTERMEDIATE THEREOF

TECHNICAL FIELD

The present invention relates to a process for producing a quinolinecarboxyaldehyde derivative particularly useful as an intermediate of cholesterol lowering agents (HMG-CoA reductase inhibitors). Particularly, it relates to a process for producing 2-cyclopropyl-4-(4'-fluorophenyl)quinoline-3-carboxylaldehyde.

BACKGROUND ART

As a process for producing a quinolinecarboxyaldehyde derivative, JP-A-1-279866, EP-A-304063 and U.S. Pat. No. 5,011,930 disclose a process which comprises reacting 2-amino-4'-fluorobenzophenone with ethyl isobutyrylacetate to obtain a quinolinecarboxylate derivative, once reducing it with diisobutylaluminum hydride to obtain a quinolinemethanol derivative, and further oxidizing it with pyridinium chlorochromate to obtain an aimed quinolinecarboxyaldehyde derivative. However, this production process comprises a large number of steps and is not advantageous as an industrial production process.

The present invention is to provide a process which makes it possible to produce 2-cyclopropyl-4-(4'-fluorophenyl)quinoline-3-carboxyaldehyde of the following formula by an industrially advantageous simple process.

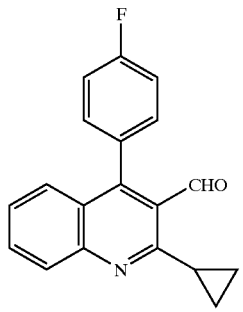

DISCLOSURE OF THE INVENTION

The present invention resides in a process for producing 2-cyclopropyl-4-(4'-fluorophenyl)quinoline-3-carboxyaldehyde, which comprises reacting 3-cyclopropyl-3-oxopropanenitrile with 2-amino-4'-fluorobenzophenone to obtain 2-cyclopropyl-4-(4'-fluorophenyl)quinoline-3-carbonitrile, and reducing it, preferably in the presence of an acid. In the production process, it is preferred to employ an organic sulfonic acid as the acid.

The present invention further resides in a process for producing 2-cyclopropyl-4-(4'-fluorophenyl)quinoline-3-carboxyaldehyde, which comprises reducing 2-cyclopropyl-4-(4'-fluorophenyl)quinoline-3-carbonitrile.

The above 2-cyclopropyl-4-(4'-fluorophenyl)quinoline-3-carbonitrile is a novel substance, and it may be obtained, for example, by employing a process of reacting 3-cyclopropyl-3-oxopropanenitrile with 2-amino-4'-fluorobenzophenone, preferably in the presence of an acid.

The process for producing 2-cyclopropyl-4-(4'-fluorophenyl)quinoline-3-carboxyaldehyde of the present invention proceeds in accordance with the following reaction path.

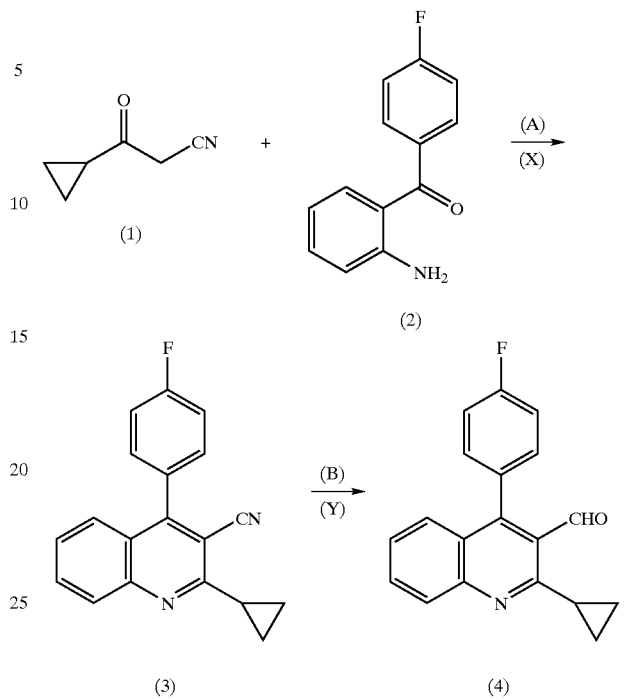

(X): Cyclization, (Y) Reduction

Now, each reaction employed in the above reaction path will be explained below.

(A) Cyclization Reaction Step

The cyclization reaction step of the present invention is a step of reacting 3-cyclopropyl-3-oxopropanenitrile of the formula (1) with 2-amino-4'-fluorobenzophenone of the formula (2) preferably in the presence of an acid to obtain a quinolinecarbonitrile derivative [2-cyclopropyl-4-(4'-fluorophenyl)quinoline-3-carbonitrile] of the formula (3).

Examples of the acid preferably employed in the above cyclization reaction step include organic sulfonic acids such as methanesulfonic acid, ethanesulfonic acid, benzenesulfonic acid, p-bromobenzenesulfonic acid and p-toluenesulfonic acid; inorganic acids such as phosphoric acid, pyrophosphoric acid, polyphosphoric acid, sulfuric acid and hydrochloric acid; and halogenated organic carboxylic acids such as monochloroacetic acid, dichloroacetic acid and trifluoroacetic acid. An organic sulfonic acid is particularly preferred.

The amount of the acid used in the cyclization reaction step is preferably from 0.1 to 5.0 mol, more preferably from 0.5 to 4.0 mol, particularly preferably from 1.0 to 3.0 mol, per 1 mol of 2-amino-4'-fluorobenzophenone.

The amount of 3-cyclopropyl-3-oxopropanenitrile used is preferably from 0.8 to 2.0 mol, more preferably from 1.0 to 1.5 mol, per 1 mol of 2-amino-4'-fluorobenzophenone.

The cyclization reaction step of the present invention is carried out in the presence or absence of a solvent. When a solvent is employed, the type of the solvent is not particularly limited so long as it does not inhibit the reaction. Examples of the solvent which may be used include aliphatic hydrocarbons such as pentane, hexane, heptane, 2-methylbutane, 2-methylpentane, 2-methylhexane, cyclopentane, cyclohexane and cycloheptane; halogenated aliphatic hydrocarbons such as methylene chloride, chloroform and dichloroethane; aromatic hydrocarbons such as benzene, toluene, xylene and mesitylene; halogenated aromatic hydrocarbons such as chlorobenzene and dichlorobenzene; ethers such as diisopropyl ether, tetrahydrofuran and dioxane, alcohols such as methanol, ethanol, isopropyl alcohol, 2-butyl alcohol and t-butyl alcohol; and organic carboxylic acids such as acetic acid and propionic acid.

The amount of the solvent used is preferably from 2 to 50 parts by mass, more preferably from 3 to 10 parts by mass, per 1 part by mass of 2-amino-4'-fluorobenzophenone. These solvents may be used alone or in combination as a mixture of at least two.

The cyclization reaction step of the present invention is preferably carried out by contacting 2-amino-4'-fluorobenzophenone with 3-cyclopropyl-3-oxopropanenitrile in a liquid phase preferably in the presence of an acid. For example, it is carried out by e.g. a method of mixing an acid, 3-cyclopropyl-3-oxopropanenitrile, 2-amino-4'-fluorobenzophenone and a solvent, followed by stirring under heating in an atmosphere of nitrogen, under normal pressure, under pressure or under reduced pressure. In such a case, the reaction temperature is preferably from 50 to 160° C., more preferably from 70 to 140° C. Further, the cyclization reaction may be carried out while removing water formed during the reaction, as the case requires. 2-Amino-4'-fluorobenzophenone may be introduced to the reaction system in such a state that it forms a salt with the above acid (for example, it may be introduced as 2-amino-4'-fluorobenzophenone methanesulfonate).

The quinolinecarbonitrile derivative [2-cyclopropyl-4-(4'-fluorophenyl)quinoline-3-carbonitrile] of the above formula (3) obtained by the above cyclization reaction step is a novel compound, and may be taken out by a common separation/purification method by e.g. distillation, recrystallization or column chromatography after completion of the reaction for example.

(B) Reduction Reaction Step

The reduction reaction step employed in the present invention is a step of reducing the quinolinecarbonitrile derivative of the formula (3) to obtain a quinolinecarboxyaldehyde derivative of the formula (4).

The above reduction reaction step is carried out by employing a common reduction method which converts a cyano group into a formyl group. For example, reduction with an aluminum hydride compound (such as diisobutylaluminum hydride), reduction with hydrogen, formic acid or ammonium formate in the presence of Raney nickel, reduction with stannous chloride, or reduction with hydrogen in the presence of palladium, may be employed. Preferably, reduction with diisobutylaluminum hydride (hereinafter referred to as reduction reaction
(a)), reduction with formic acid in the presence of Raney nickel (hereinafter referred to as reduction reaction
(b)) or reduction with hydrogen in the presence of Raney nickel (hereinafter referred to as reduction reaction
(c)) is employed.

(1) Reduction Reaction (a): Reduction With Diisobutylaluminum Hydride

The amount of diisobutylaluminum hydride used in the reduction reaction (a) is preferably from 0.5 to 5.0 mol, more preferably from 0.9 to 1.5 mol, per 1 mol of the quinolinecarbonitrile derivative.

The reduction reaction (a) is carried out in the presence or absence of a solvent. The solvent used is not particularly limited so long as it does not inhibit the reaction, and examples of which include aromatic hydrocarbons such as benzene, toluene and xylene; and ethers such as diisopropyl ether, tetrahydrofuran and dioxane. Preferably an aromatic hydrocarbon, more preferably toluene is employed.

The amount of the solvent used is preferably from 2 to 50 parts by mass, more preferably from 3 to 20 parts by mass, per 1 part by mass of the quinolinecarbonitrile derivative. These solvents may be used alone or in combination as a mixture of at least two.

The reduction reaction (a) is carried out preferably by contacting diisobutylaluminum hydride with the quinolinecarbonitrile derivative in a liquid phase. For example, it is carried out by e.g. a method of mixing diisobutylaluminum hydride, the quinolinecarbonitrile derivative and a solvent preferably under cooling and reacting them in an atmosphere of an inert gas, under normal pressure or under pressure. In such a case, the reaction temperature is preferably from −50 to 60° C., more preferably from −20 to 40° C.

(2) Reduction Reaction (b): Reduction with Formic Acid in the Presence of Raney Nickel The Raney nickel employed in the reduction reaction (b) is an alloy containing nickel and aluminum as the main components, and one having a nickel content of preferably from 10 to 90 mass %, more preferably from 40 to 80 mass %, is employed. Usually expanded Raney nickel is employed, but Raney nickel subjected to a pretreatment by various methods or stabilized Raney nickel may also be employed. Further, one containing a metal such as cobalt, iron, lead, chromium, titanium, molybdenum, vanadium, manganese, tin or tungsten in Raney nickel may also be employed.

The amount of the Raney nickel used is preferably from 0.30 to 2 parts by mass, more preferably from 0.30 to 1.2 parts by mass, as calculated as nickel atoms, per 1 part by mass of the quinolinecarbonitrile derivative.

The formic acid employed in the reduction reaction (b) may be used as formic acid alone, however, preferably the reaction is carried out in the presence of formic acid and water in an amount of from 0.25 to 1 part by volume per 1 part by volume of formic acid.

The amount of formic acid used is preferably from 0.25 to 50 parts by mass, more preferably from 1 to 40 parts by mass, per 1 part by mass of the quinolinecarbonitrile derivative.

The reduction reaction (b) may be carried out in the presence of a solvent other than formic acid and water. The solvent which may be employed is not particularly limited so long as it does not inhibit the reaction, and examples of which include amides such as N,N-dimethylformamide; alcohols such as methanol, ethanol, isopropyl alcohol and t-butyl alcohol; aliphatic hydrocarbons such as pentane and cyclohexane; aromatic hydrocarbons such as toluene and xylene; and organic carboxylic acids such as acetic acid and propionic acid.

The amount of the solvent used is preferably from 0 to 60 parts by mass, more preferably from 0 to 10 parts by mass, per 1 part by mass of the quinolinecarbonitrile derivative. These solvents may be used alone or in combination as a mixture of at least two.

The reduction reaction (b) is carried out preferably by contacting formic acid and water with the quinolinecarbonitrile derivative in a liquid phase in the presence of Raney nickel. For example, it is carried out by e.g. a method of mixing Raney nickel, the quinolinecarbonitrile derivative, formic acid and water, followed by stirring under heating in an atmosphere of an inert gas, under normal pressure or under pressure. In such a case, the reaction temperature is preferably from 20 to 110° C., more preferably from 30 to 80° C.

Further, as the case requires, e.g. an inorganic base, an organic base, a platinum salt, a lead salt or a cadmium salt may be added to the reaction system to adjust the reactivity [Teruo Kubomatsu, Shinichiro Komatsu, "Raney catalyst" (published by Kawaken Fine Chemicals Co., Ltd.), p. 123–147, HU 45958].

The quinolinecarboxyaldehyde derivative as a final product is separated and purified by a common method such as distillation, recrystallization or column chromatography after completion of the reaction for example.

(3) Reduction Reaction (c): Reduction with Hydrogen in the Presence of Raney Nickel The Raney nickel employed in the reduction reaction (c) is an alloy containing nickel and aluminum as the main components, and one having a nickel content of preferably from 10 to 90 mass %, more preferably from 40 to 80 mass %, is employed. Usually expanded Raney nickel is employed, but Raney nickel subjected to a pretreatment by various methods or stabilized Raney nickel may also be employed. Further, one containing a metal such as cobalt, iron, lead, chromium, titanium, molybdenum, vanadium, manganese, tin or tungsten in Raney nickel may also be employed.

The amount of the Raney nickel used is preferably from 0.001 to 2 parts by mass, more preferably from 0.01 to 1.2 parts by mass, as calculated as nickel atoms, per 1 part by mass of the quinolinecarbonitrile derivative.

The reduction reaction (c) is carried out preferably in the presence of an acid, and sulfuric acid, methanesulfonic acid, acetic acid or trifluoroacetic acid may, for example, be employed. The amount used is preferably from 1 to 10 mol, more preferably from 1.5 to 5 mol, per 1 mol of the quinolinecarbonitrile derivative.

The reduction reaction (c) is carried out in a solvent. The solvent used is not particularly limited so long as it does not inhibit the reaction, and examples of which include water; alcohols such as methanol, ethanol, isopropyl alcohol and t-butyl alcohol; amides such as N,N-dimethylformamide; aliphatic hydrocarbons such as pentane and cyclohexane; aromatic hydrocarbons such as toluene and xylene; carboxylic acids such as formic acid, acetic acid and propionic acid; and ethers such as diisopropyl ether, tetrahydrofuran and dioxane.

The amount of the above solvent used is preferably from 1 to 50 parts by mass, more preferably from 2 to 20 parts by mass, per 1 part by mass of the quinolinecarbonitrile derivative. These solvents may be used alone or in combination as a mixture of at least two.

The reduction reaction (c) is preferably carried out by contacting hydrogen with the quinolinecarbonitrile derivative in a liquid phase in the presence of Raney nickel. For example, it is carried out by e.g. a method of mixing Raney nickel, the quinolinecarbonitrile derivative and a solvent, followed by stirring with heating, in an atmosphere of hydrogen (which may be diluted with an inert gas), under a pressure of from 0.1 to 5 MPa, as closed or while circulating hydrogen. In such a case, the reaction temperature is preferably from 10 to 100° C., more preferably from 20 to 70° C.

As the case requires, e.g. an inorganic base, an organic base, a platinum salt, a lead salt or a cadmium salt may be added to the reaction system to adjust the reactivity [Teruo Kubomatsu, Shinichiro Komatsu, "Raney catalyst" (published by Kawaken Fine Chemicals Co., Ltd.), p. 123–147, HU 45958].

The quinolinecarboxyaldehyde derivative as a final product is separated and purified by a common method such as distillation, recrystallization or column chromatography after completion of the reaction for example.

Now, the present invention will be explained in further detail with reference to Examples.

EXAMPLE 1

Into a glass flask having an internal volume of 200 mL, equipped with a stirring apparatus, a thermometer, a reflux condenser and a Dean-Stark apparatus, 80 mL of toluene and 20 mL of cyclohexane were put in an atmosphere of nitrogen, and 2.94 g (30.6 mmol) of methanesulfonic acid, 3.50 g (32.1 mmol) of 3-cyclopropyl-3-oxopropanenitrile and 6.59 g (30.6 mmol) of 2-amino-4'-fluorobenzophenone were added thereto with stirring. Then, the temperature was raised, and reaction was carried out at a temperature of from 90 to 95° C. for 4 hours while distilling off the formed water. After completion of the reaction, the reaction liquid was cooled to room temperature, and 100 mL of water and 5.5 mL (44.0 mmol) of 8 mol/L sodium hydroxide aqueous solution were added to make the reaction liquid basic. The obtained reaction liquid was extracted with 200 mL of ethyl acetate twice, then the organic layer was separated, and 2 g of anhydrous magnesium sulfate, 2 g of silica gel and 2 g of activated carbon were added, followed by stirring at room temperature for 1 hour. After filtration, the filtrate was concentrated under reduced pressure to obtain 8.45 g of 2-cyclopropyl-4-(4'-fluorophenyl)quinoline-3-carbonitrile as a pale yellow solid with a purity of 99% (area percentage by high performance liquid chromatography) (yield: 95%).

Physical properties of the obtained 2-cyclopropyl-4-(4'-fluorophenyl)quinoline-3-carbonitrile were as follows:

Melting point: 161.0–161.5° C. Elemental analysis: carbon 79.17%, hydrogen 4.54%, nitrogen 9.76% [Theoretical values ($C_{19}H_{13}N_2F$):carbon 79.15%, hydrogen 4.54%, nitrogen 9.72%]CI-MS(m/e): 289(M+1) IR(KBr method, $cm^{-1}$): 2225,1605,1561,1514,1493,1222, 1162,846,769 $^1$H-NMR (CDCl$_3$, δ (ppm)): 1.71–1.24(2H,m) , 1.37–1.43(2H,m), 2.66–2.72(1H,m), 7.25–7.32(2H,m), 7.41–7.49(3H,m), 7.58 (1H,d,J=6.8 Hz), 7.72–7.79(1H,m), 7.99(1H,d,J=8.5Hz)

EXAMPLE 2

Into a glass flask having an internal volume of 10 mL, equipped with a stirring apparatus, a thermometer, a reflux condenser and a Dean-Stark apparatus, 5 mL of diisopropyl ether was put in an atmosphere of nitrogen, and 0.82 g (4.6 mmol) of pyrophosphoric acid, 0.29 g (2.5 mmol) of 3-cyclopropyl-3-oxopropanenitrile and 0.50 g (2.3 mmol) of 2-amino-4'-fluorobenzophenone were added thereto with stirring at room temperature. Then, the temperature was raised to 70° C., and reaction was carried out for 3 hours. After completion of the reaction, the reaction liquid was cooled to room temperature, and analyzed by high performance liquid chromatography (absolute quantitative analysis), whereupon 0.60 g (yield: 91%) of 2-cyclopropyl-4-(4'-fluorophenyl)quinoline-3-carbonitrile was formed.

EXAMPLE 3

The reaction was carried out in the same manner as in Example 2 except that the solvent was changed to dichloroethane, and the reaction temperature and the reaction time were changed to 70° C. for 3 hours and 90° C. for 3 hours. As a result, 0.54 g (yield: 82%) of 2-cyclopropyl-4-(4'-fluorophenyl)quinoline-3-carbonitrile was formed.

EXAMPLE 4

The reaction was carried out in the same manner as in Example 2 except that the acid was changed to 0.66 g (7.0 mmol) of monochloroacetic acid, and the reaction time was changed to 9 hours. As a result, 0.40 g (yield: 60%) of 2-cyclopropyl-4-(4'-fluorophenyl)quinoline-3-carbonitrile was formed.

EXAMPLE 5

The reaction was carried out in the same manner as in Example 2 except that the acid was changed to 0.22 g (2.3 mmol) of 96 mass % sulfuric acid, and the solvent was changed to 2-butanol. As a result, 0.49 g (yield: 75%) of 2-cyclopropyl-4-(4'-fluorophenyl)quinoline-3-carbonitrile was formed.

EXAMPLE 6

Into a glass flask having an internal volume of 50 mL, equipped with a stirring apparatus, a thermometer and a reflux condenser, 0.72 g (6.6 mmol) of 3-cyclopropyl-3-oxopropanenitrile, 1.92 g (6.0 mmol) of 2-amino-4'-fluorobenzophenone methanesulfonate having a purity of 97.3% and 10 mL of toluene were put in an atmosphere of nitrogen, and reaction was carried out at 80° C. for 2 hours. After completion of the reaction, the reaction liquid was cooled to room temperature, 7.0 mL (7.0 mmol) of a 1 mol/L sodium hydroxide aqueous solution was added thereto to make the reaction liquid basic, followed by liquid separation, and the obtained organic layer was analyzed by high performance liquid chromatography (absolute quantitative analysis), whereupon 1.70 g (yield: 98%) of 2-cyclopropyl-4-(4'-fluorophenyl)quinoline-3-carbonitrile was formed.

EXAMPLE 7

Into a glass flask having an internal volume of 300 mL, equipped with a stirring apparatus, a thermometer, a reflux condenser and a Dean-Stark apparatus, 11.6 g (106.6 mmol) of 3-cyclopropyl-3-oxopropanenitrile, 31.0 g (96.9 mmol) of 2-amino-4'-fluorobenzophenone methanesulfonate having a purity of 97.3% and 121 mL of toluene were put in an atmosphere of nitrogen, and reaction was carried out under 0.04 MPa at 80° C. for 2 hours while distilling off the formed water. After completion of the reaction, the reaction liquid was cooled to room temperature, 60 mL of water and 13.3 mL (106.4 mmol) of a 8 mol/L sodium hydroxide aqueous solution were added thereto to make the reaction liquid basic, followed by liquid separation, and the obtained organic layer was analyzed by high performance liquid chromatography (absolute quantitative analysis), whereupon 27.9 g (yield: 99%) of 2-cyclopropyl-4-(4'-fluorophenyl)quinoline-3-carbonitrile was formed.

EXAMPLE 8

Into a glass flask having an internal volume of 50 mL, equipped with a stirring apparatus, a thermometer, a reflux condenser and a Dean-Stark apparatus, 10.72 g (6.6 mmol) of 3-cyclopropyl-3-oxopropanenitrile, 1.92 g (6.0 mmol) of 2-amino-4'-fluorobenzophenone methanesulfonate having a purity of 97.3% and 10 mL of toluene were put in an atmosphere of nitrogen, and reaction was carried out under at 110° C. for 2 hours while distilling off the formed water. After completion of the reaction, the reaction liquid was cooled to room temperature, 7.0 mL (7.0 mmol) of a 1 mol/L sodium hydroxide aqueous solution was added thereto to make the reaction liquid basic, followed by liquid separation, and the obtained organic layer was analyzed by high performance liquid chromatography (absolute quantitative analysis), whereupon 1.57 g (yield: 91%) of 2-cyclopropyl-4-(4'-fluorophenyl)quinoline-3-carbonitrile was formed.

EXAMPLE 9

Into a glass flask having an internal volume of 50 mL, equipped with a stirring apparatus, a thermometer and a dropping funnel, 0.29 g (1.0 mmol) of 2-cyclopropyl-4-(4'-fluorophenyl)quinoline-3-carbonitrile produced in Example 1 and 2.5 mL of toluene were put in an atmosphere of argon, and cooled to −10° C. in an ice bath. Then, while maintaining the liquid temperature at from −10 to 0° C., 0.68 mL (1.0 mmol) of a 1.5 mol/L diisobutylaluminum hydride toluene solution was dropwise added thereto gradually. After completion of the dropwise addition, the temperature was raised to room temperature, followed by stirring for 1 hour. After completion of the reaction, 1 mL of methanol was added to the obtained reaction liquid, followed by stirring for 10 minutes, and 15 mL of 1 mol/L hydrochloric acid was added thereto for neutralization. Then, the reaction liquid was concentrated under reduced pressure, 15 mL of water was added thereto, and extraction with 30 mL of chloroform was carried out three times. Then, the organic layer was separated and recovered, and dried over anhydrous magnesium sulfate. After filtration, the filtrate was concentrated under reduced pressure to obtain 0.30 g of 2-cyclopropyl-4-(4'-fluorophenyl)quinoline-3-carboxyaldehyde as a yellow solid with a purity of 99% (area percentage by high performance liquid chromatography) (yield: 88%).

Physical properties of the obtained 2-cyclopropyl-4-(4'-fluorophenyl)quinoline-3-carboxyaldehyde were as follows.

CI-MS(m/e): 292(M+1) $^1$H-NMR(CDCl$_3$, δ (ppm)): 1.07–1.13(2H,m), 1.36–1.58(2H,m), 3.19–3.24(1H,m), 7.23–7.72(6H,m), 7.73–7.77(1H,m), 7.97(1H,d,J=8.7 Hz), 10.07(1H,s)

EXAMPLE 10

Into a glass flask having an internal volume of 5 mL, equipped with a stirring apparatus, a thermometer and a dropping funnel, 500 mg (1.7 mmol) of 2-cyclopropyl-4-(4'-fluorophenyl)quinoline-3-carbonitrile produced in Example 1, 5.0 mL (141 mmol) of a 95 vol % formic acid aqueous solution and 750 mg (6.4 mmol as nickel atoms) of hydrated expanded Raney nickel (manufactured by Kawaken Fine Chemicals Co., Ltd., NDHT-90 (nickel content: 50 mass %)) were put in an atmosphere of nitrogen, and a reaction was carried out at 40° C. for 7 hours. After completion of the reaction, the reaction liquid was cooled to room temperature, the catalyst was filtered out with celite, and the reaction liquid was concentrated. Then, 5 mL of 1 mol/L hydrochloric acid was added to the obtained concentrate, and extraction with 50 mL of toluene was carried out twice. The organic layer was separated and analyzed by high performance liquid chromatography (absolute quantitative analysis), whereupon 218 mg (yield: 43%) of 2-cyclopropyl-4-(4'-fluorophenyl)quinoline-3-carboxyaldehyde was formed.

EXAMPLE 11

Into a polycarbonate autoclave having an internal volume of 100 mL, equipped with a stirring apparatus, 300 mg (1.0 mmol) of 2-cyclopropyl-4-(4'-fluorophenyl)quinoline-3-carbonitrile produced in Example 1, 526 mg (5.2 mmol) of 97 mass % sulfuric acid, 150 mg (1.3 mmol as nickel atoms) of hydrated expanded Raney nickel (manufactured by Kawaken Fine Chemicals Co., Ltd.: NDHT-90 (nickel content: 50 mass %)) and 15 mL of ethanol were added, and a reaction was carried out under a hydrogen pressure of from 0.2 to 0.4 MPa at room temperature for 2 hours. The obtained reaction liquid was analyzed by high performance liquid chromatography (absolute quantitative analysis), whereupon 105 mg (yield: 36%) of 2-cyclopropyl-4-(4'-fluorophenyl)quinoline-3-carboxyaldehyde was formed.

Industrial Applicability

According to the present invention, a quinolinecarboxyaldehyde derivative can be obtained with a high yield by using an easily available compound by a simple process. Accordingly, the process for producing a quinolinecarboxyaldehyde derivative of the present invention is industrially advantageous.

What is claimed is:

1. A process for producing 2-cyclopropyl-4-(4'-fluorophenyl)quinoline-3-carboxyaldehyde, which comprises reacting 3-cyclopropyl-3-oxopropanenitrile with 2-amino-4'-fluorobenzophenone to obtain 2-cyclopropyl-4-(4'-fluorophenyl)quinoline-3-carbonitrile, and reducing it.

2. The production process according to claim 1, wherein the reaction of 3-cyclopropyl-3-oxopropanenitrile with 2-amino-4'-fluorobenzophenone is carried out in the presence of an acid.

3. The production process according to claim 2, wherein an organic sulfonic acid is employed as the acid.

4. A process for producing 2-cyclopropyl-4-(4'-fluorophenyl)quinoline-3-carboxyaldehyde, which comprises reducing 2-cyclopropyl-4-(4'-fluorophenyl)quinoline-3-carbonitrile.

5. 2-Cyclopropyl-4-(4'-fluorophenyl)quinoline-3-carbonitrile.

6. A process for producing 2-cyclopropyl-4-(4'-fluorophenyl)quinoline-3-carbonitrile, which comprises reacting 3-cyclopropyl-3-oxopropanenitrile with 2-amino-4'-fluorobenzophenone.

7. The production process according to claim 6, wherein the reaction of 3-cyclopropyl-3-oxopropanenitrile with 2-amino-4'-fluorobenzophenone is carried out in the presence of an acid.

8. The production process according to claim 7, wherein an organic sulfonic acid is employed as the acid.

* * * * *